(12) United States Patent
Siegfried et al.

(10) Patent No.: US 9,593,153 B2
(45) Date of Patent: Mar. 14, 2017

(54) MODIFIED APELIN POLYPEPTIDES

(71) Applicants: INSERM (INSTITUT NATIONAL DE LA SANTE ET DE LA RECHERCHE MEDICALE), Paris (FR); UNIVERSITE PARIS-SUD XI, Orsay (FR); UNIVERSITE DE BORDEAUX, Bordeaux (FR)

(72) Inventors: Geraldine Siegfried, Kremlin Bicetre (FR); Abdel-Majid Khatib, Talence (FR)

(73) Assignees: INSERM (INSTITUT NATIONAL DE LA SANTE ET DE LA RECHERCHE MEDICALE), Paris (FR); UNIVERSITE PARIS-SUD XI, Orsay (FR); UNIVERSITE DE BORDEAUX, Bordeaux (FR)

( * ) Notice: Subject to any disclaimer, the term of this patent is extended or adjusted under 35 U.S.C. 154(b) by 0 days.

(21) Appl. No.: 14/391,404

(22) PCT Filed: Apr. 9, 2013

(86) PCT No.: PCT/EP2013/057356
§ 371 (c)(1),
(2) Date: Oct. 9, 2014

(87) PCT Pub. No.: WO2013/153049
PCT Pub. Date: Oct. 17, 2013

(65) Prior Publication Data
US 2015/0072932 A1   Mar. 12, 2015

(30) Foreign Application Priority Data

Apr. 11, 2012   (EP) .................... 12305426

(51) Int. Cl.
*A61K 38/18*   (2006.01)
*C07K 14/475*   (2006.01)
*C12N 5/10*   (2006.01)
*C12N 1/21*   (2006.01)
*C12N 15/63*   (2006.01)
*C07K 14/575*   (2006.01)
*C07K 14/47*   (2006.01)

(52) U.S. Cl.
CPC ............ *C07K 14/575* (2013.01); *C07K 14/47* (2013.01)

(58) Field of Classification Search
None
See application file for complete search history.

(56) References Cited

U.S. PATENT DOCUMENTS

2010/0221255 A1   9/2010   Cuttitta et al.

OTHER PUBLICATIONS

"Predicted: Pan troglodytes apelin (APLN), mRNA", Database Nucleotide, May 13, 2011, Web.
"SubName: Full=LOC100135238 protein; Subname: Full=uncharacterized protein", Database UniProt, Feb. 5, 2008, Web.
Pitkin et al., "International Union of Basic and Clinical Pharmacology. LXXIV. Apelin Receptor Nomenclature, Distribution, Pharmacology, and Function", Pharmacological Reviews, Sep. 1, 2010, pp. 331-342, vol. 62, No. 3.
Tatemoto et al., "Isolation and Characterization of a Novel Endogenous Peptide Ligand for the Human APJ Receptor", Biochemical and Biophysical Research Communications, Jan. 1, 1998, pp. 471-476, vol. 251, No. 2.
Habata et al., "Apelin, the natural ligand of the orphan receptor APJ, is abundantly secreted in the colostrum", Biochimica Et Biophysica Acta. Molecular Cell Research, Oct. 13, 1999, pp. 25-35, vol. 1452, No. 1.

*Primary Examiner* — Christine J Saoud
(74) *Attorney, Agent, or Firm* — Whitham, Curtis & Cook, P.C.

(57) ABSTRACT

The present invention relates to polypeptides and their uses as apelin inhibitors. More particularly, the present invention relates to a polypeptide comprising the sequence as set forth in SEQ ID NO:1 wherein at least one arginine residue at position 18, 19, 22 or 23 has been substituted or deleted.

5 Claims, 5 Drawing Sheets

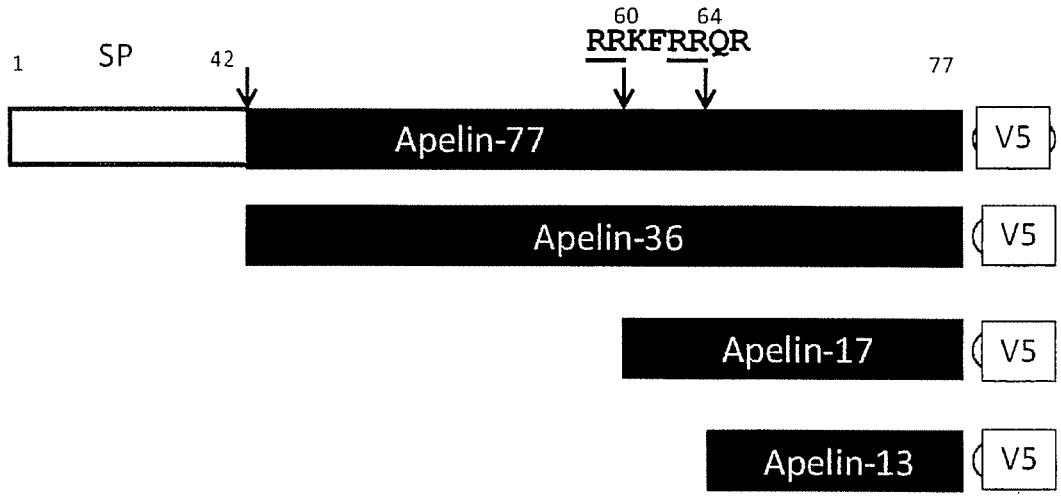

Figure 1A

Figure 2:
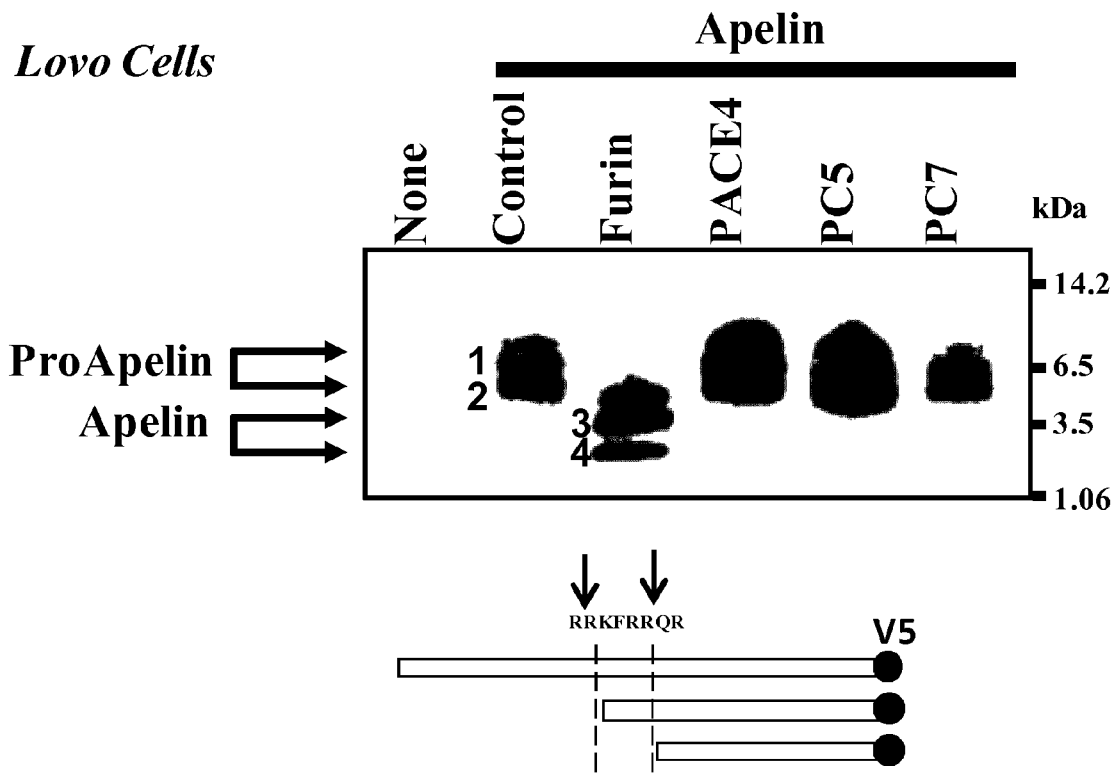

```
mouse      MILRLCVQALLLLWLSLTAVCGVPLMLPPDGTGLEE-GSMRYLVKPRTSRTGPGAWQGGR 59
rat        MILSFCVQALLLLWLSLTAVCGVPLMLPPDGKGLEE-GMMRYLVKPRTSRTGPGAWQGGR 59
human      MILRLCVQALLLLWLSLTAVCGGSLMPLPDGNGLED-GIVRHLVQPRGSRIGPGPWQGGR 59
bovine     MILRRCVQALLLLWLCLSAVCGGPLLQTSDGKEMEE-GTIRYLVQPRGPRSGPGPWQGGR 59
zebrafish  MIVKILTLVIVLVVSLLCSASAGPMASTEHSKEIEEVGSMRTPLRQNPARAGRSQRPAGW 60
goldfish   MIVKILTLVIVLVVSLLCSASAGPMASTEHSKELEEVGSMRTPLRQNPARAGRSQRPSGW 60
           **:    . .::*:   *  :... .:    ... :*: *.:*  ::  .* *  .  .* mouse      RKFRRQRPRLSHKGPMPF 77
rat        RKFRRQRPRLSHKGPMPF 77
human      RKFRRQRPRLSHKGPMPF 77
bovine     RKFRRQRPRLSHKGPMPF 77
zebrafish  RR-RRPRPRLSHKGPMPF 77
goldfish   RR-RRPRPRLSHKGPMPF 77
           *: ** ***********+
```

Figure 1B

MODIFIED APELIN POLYPEPTIDES

FIELD OF THE INVENTION

The present invention relates to polypeptides and their uses as apelin inhibitors.

BACKGROUND OF THE INVENTION

The orphan receptor APJ (putative receptor protein related to angiotensin II type 1 receptor or AT1) is a G-protein coupled receptor with seven transmembrane domains, constituted of 380 amino acids. In the search for an endogenous ligand of the orphan receptor APJ, a peptide called apelin (APJ endogenous ligand) was first isolated from bovine stomach extracts and the corresponding human protein was deduced from this discovery.

The apelin polypeptide is initially produced as a 77 amino acid protein (called preproapelin) that is cleaved to produce cleavage products of 36 amino acids (proapelin), 17 amino acids, and 13 amino acids, each of them having a high affinity (in the nM range) for the APJ receptor. The peptide size of apelin-17 and apelin-13 are necessary and sufficient for the ability of an apelin polypeptide to interact with APJ. Currently, the mechanism and function of apelin precursor (proapelin or apelin-36) conversion to mature apelin peptides (apelin-17 or apelin-13) are not well known.

Apelin and APJ receptors are both widely distributed in the brain but are particularly highly expressed in the supraoptic (SON) and paraventricular (PVN) hypothalamic nuclei. Dual labelling studies demonstrate that within these two nuclei, apelin and its receptor are colocalized with vasopressin (AVP) in a subset of magnocellular neurons. In lactating rats, characterized by increases in both synthesis and release of AVP, central injection of apelin inhibits the phasic electrical activity of AVP neurons, decreases systemic AVP release inducing aqueous diuresis. Taken together, these data suggest that apelin is a natural inhibitor of the antidiuretic effect of AVP. Moreover apelin systemically administered reduces arterial blood pressure, increases cardiac contractility and reduces cardiac loading.

SUMMARY OF THE INVENTION

The present invention relates to a polypeptide comprising the sequence as set forth in SEQ ID NO:1 [APELIN-36] wherein at least one arginine residue at position 18, 19, 22 or 23 has been substituted or deleted.

DETAILED DESCRIPTION OF THE INVENTION

The present invention relates to a polypeptide comprising the sequence as set forth in SEQ ID NO:1 [APELIN-36] wherein at least one arginine residue at position 18, 19, 22 or 23 has been substituted or deleted.

In one embodiment, the polypeptide according to the invention comprises a sequence as set forth in SEQ ID NO:2 [APELIN-77] wherein at least one arginine residue at position 59, 60, 63, or 64 has been substituted or deleted.

According to one embodiment, 1, 2, 3, or 4 arginine residues are substituted or deleted.

The Arginine residue substitution(s) may be performed with any amino acid that leads to the deletion of the cleavage site and the generation of unprocessed form of apelin. Typically, the arginine residue(s) may be substituted independently by a neutral amino acid selected from the group consisting of asparagine, glutamine, serine, threonine, tyrosine, glycine, alanine, valine, leucine, isoleucine, proline, phenylalanine, methionine and tryptophane. In a particular embodiment, the arginine residues are independently substituted by a serine residue and in another particular embodiment all arginine residues are substituted by a serine residue.

The polypeptides of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

A further object of the present invention encompasses function-conservative variants of the polypeptides of the present invention, providing that the at least one arginine residue at position 18, 19, 22 or 23 remains deleted or substituted. "Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 85%, and even more preferably at least 90%, and which has the same or substantially similar properties or functions as the native or parent protein to which it is compared.

In a particular embodiment, the polypeptide of the invention consists or comprises a sequence having at least 90% amino acid identity with SEQ ID NO:1 providing that the arginine residues at position 18, 19, 22 or 23 has been substituted or deleted.

In a particular embodiment, the polypeptide of the invention consists or comprises a sequence having at least 90% amino acid identity with SEQ ID NO:2 providing that the arginine residues at position 59, 60, 63, or 64 has been substituted or deleted.

In one embodiment, the polypeptide according to the invention comprises a sequence as set forth in SEQ ID NO:3 (Apelin-77 mouse) wherein at least one arginine residue at position 59, 60, 63, or 64 has been substituted or deleted.

In one embodiment, the polypeptide according to the invention comprises a sequence as set forth in SEQ ID NO:4

(Apelin-77 rat) wherein at least one arginine residue at position 59, 60, 63, or 64 has been substituted or deleted.

In one embodiment, the polypeptide according to the invention comprises a sequence as set forth in SEQ ID NO:5 (Apelin-77 bovine) wherein at least one arginine residue at position 59, 60, 63, or 64 has been substituted or deleted.

In one embodiment, the polypeptide of the invention consists or comprises a sequence having at least 90% amino acid identity with SEQ ID NO:8 (LVQPRGSRNGPGP-WQGGSSKFSSQRPRLSHKGPMPF).

In one embodiment, the polypeptide of the invention consists or comprises a sequence as set forth in SEQ ID NO:8 (LVQPRGSRNGPGPWQGGSSKFSSQRPRLSHK-GPMPF).

Polypeptides of the invention can be use in an isolated (e.g., purified) form or contained in a vector, such as a membrane or lipid vesicle (e.g. a liposome).

A further object of the invention relates to a nucleic acid comprising a sequence encoding for a polypeptide of the invention.

Typically, said nucleic acid is a DNA or RNA molecule, which may be included in any suitable vector, such as a plasmid, cosmid, episome, artificial chromosome, phage or a viral vector. The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said polypeptide upon administration to a subject. The vectors may further comprise one or several origins of replication and/or selectable markers. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like.

Examples of plasmids include replicating plasmids comprising an origin of replication, or integrative plasmids, such as for instance pUC, pcDNA, pBR, and the like. Examples of viral vector include adenoviral, retroviral, herpes virus and AAV vectors. Such recombinant viruses may be produced by techniques known in the art, such as by transfecting packaging cells or by transient transfection with helper plasmids or viruses.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.).

The present invention also relates to a method for producing a recombinant host cell expressing a polypeptide according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said polypeptide. Such recombinant host cells can be used for the production of polypeptides according to the present invention, as previously described.

The invention further relates to a method of producing a polypeptide according to the invention, which method comprises the steps consisting of: (i) culturing a transformed host cell according to the invention under conditions suitable to allow expression of said polypeptide; and (ii) recovering the expressed polypeptide.

In specific embodiments, it is contemplated that the polypeptides of the invention may be modified in order to improve their therapeutic efficacy. Such modification may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids may also be suitable because they retain the biocompatibility properties of PEG, but they have the added advantage of numerous attachment points per molecule (providing greater drug loading), and which could be synthetically designed to suit a variety of applications. Those of skill in the art are aware of PEGylation techniques for the effective modification of drugs. For example, drug delivery polymers that consist of alternating polymers of PEG and tri-functional monomers such as lysine have been used. The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

A further object of the invention relates to a polypeptide of the invention as an apelin inhibitor.

The role of apelin in the pathophysiology of various diseases has been described in Pitkin S L, Maguire J J, Bonner T I, Davenport A P. International Union of Basic and Clinical Pharmacology. LXXIV. Apelin receptor nomenclature, distribution, pharmacology, and function. Pharmacol Rev. 2010 September; 62(3):331-42. Epub 2010 Jul. 6. Review.

Accordingly, the polypeptides according to the invention may be suitable for the modulation of central nervous system function (vasopressin neuron activity and systemic vasopressin release, drinking behaviour, food intake), cardiovascular function (blood pressure, myocardium contractibility), immune function, gastrointestinal function, metabolic function, reproductive function, etc. . . . , and therefore, can be used as a therapeutic and/or prophylactic agent for a variety of diseases.

The present invention thus a method for treating and/or preventing a disease, condition or disorder mediated by the apelin in mammals, such method involving the step of administering to a mammal in need thereof a therapeutically effective amount of a polypeptide of the present invention or a pharmaceutical composition thereof.

Diseases, conditions and/or disorders which could be treated or prevented by the administration of a polypeptide of the invention are for example:

Inappropriate vasopressin secretions (SIADH) including pathologies like neurogenic diabetes mellitus (e.g. diabetic complications such as diabetic nephropathy, diabetic neuropathy, diabetic retinopathy, etc.), lung cancer, septic choc, thirst troubles;

Cardiovascular diseases: Heart failure, diseases of kidney (e.g. renal failure, nephritis, etc.) hypertension, cirrhosis, arteriosclerosis, pulmonary emphysema, pulmonary oedema;

Metabolic diseases: Obesity, anorexia, hyperphagia, polyphagia, hypercholesterolemia, hyperglyceridemia, hyperlipemia;

Various types of dementia such as senile dementia, cerebrovascular dementia, dementia due to genealogical denaturation degenerative diseases (e.g. Alzheimer's disease, Parkinson's disease, Pick's disease, Huntington's disease, etc.), dementia resulting from infectious diseases (e.g. delayed virus infections such as Creutzfeldt-Jakob disease), dementia associated with endocrine diseases, metabolic diseases, or poisoning (e.g. hypothyroidism, vitamin B12 deficiency, alcoholism, poisoning caused by various drugs, metals, or organic compounds), dementia caused by tumors (e.g. brain tumor), and dementia due to traumatic diseases (e.g. chronic subdural hematoma), depression, hyperactive child syndrome (microencephalopathy), disturbance of consciousness, anxiety disorder, schizophrenia, phobia;

Growth hormone secretory disorder (e.g. gigantism, acromegaly, etc.), hyperprolactinemia. galactorrhea.

Cancer (e.g. mammary cancer, lymphocytic leukemia, bladder cancer, ovary cancer, carcinoma of prostate, etc.);

And pancreatitis, Turner's syndrome, neurosis, rheumatoid arthritis, spinal cord injury, transient brain ischemia, amyotrophic lateral sclerosis, spinocerebellar degeneration, bone fracture, wounds, atopic dermatitis, osteoporosis, asthma, epilepsy, sterility.

The polypeptide of the invention may be used as a postoperative nutritional status improving agent or as an inotropic agent, vasodilatator or an aqueous diuretic.

In a particular embodiment, the polypeptide of the invention may used for the inhibition of the anti-aggregant function of apelin.

In another embodiment, the polypeptide of the invention may be used for the treatment of angiogenic diseases.

An "angiogenic disease" is a disease associated with unregulated angiogenesis. Typically, angiogenic diseases include but are not limited to primary and metastatic solid tumors, including carcinomas of breast, colon, rectum, lung, oropharynx, hypopharynx, esophagus, stomach, pancreas, liver, gallbladder and bile ducts, small intestine, kidney, bladder, urothelium, female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, such as astrocytomas, gliomas, glioblastomas, retinoblastomas, neuromas, neuroblastomas, Schwannomas, and meningiomas. Angiogenic diseases also relate to tumors arising from hematopoietic malignancies such as leukemias as well both Hodgkin's and non-Hodgkin's lymphomas. Angiogenic diseases also pertain to rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration (e.g. age-related macular degeneration), hypoxia, angiogenesis in the eye associated with infection or surgical intervention, and other abnormal neovascularization conditions of the eye. Angiogenic diseases further include skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliacjoints'; angiofibroma; and wound granulation. Other angiogenic diseases include diseases characterized by excessive or abnormal stimulation of endothelial cells, including but not limited to intestinal adhesions, Crohn's disease, atherosclerosis, scleroderma, and hypertrophic scars, i.e. keloids., diseases that have angiogenesis as a pathologic consequence such as cat scratch disease (Rochele ninalia quintosa) and ulcers (*Helicobacter pylori*).

The polypeptide of the invention is used for the reduction of angiogenesis. The amount effective to reduce angiogenesis correspond to at least a reduction of about 15%-80%, or more, when compared to control untreated subject or a placebo-treated control.

For cancer treatments, the polypeptide of the invention may be used for the treatment of both primary and metastatic tumors where the angiogenesis is a crucial process. Accordingly, the polypeptide of the invention may be useful for metastases inhibition that are originated from the tumors described above. The polypeptide of the invention may be used alone or in combination with adjunct therapy including radiotherapy and/or chemotherapy.

The polypeptide of the invention may be used in combination with any therapeutical agent. For example the polypeptide of the invention may be administered with one or more other therapeutic agents, such as cancer chemotherapeutic agent; VEGF antagonist. The polypeptide may be administered prior to, concurrently, or after other substance or therapy. The polypeptide may be administered as an adjuvant therapy to a standard cancer therapy such as surgery, radiation, bone marrow transplantation, chemotherapeutic treatment.

The polypeptide of the invention may be combined with pharmaceutically acceptable excipients, and optionally sustained-release matrices, such as biodegradable polymers, to form pharmaceutical compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptides can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The polypeptides may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. For the treatment the dose of the polypeptide that will be used depends on the severity of the disease, the age and the weight of the patient and the routes of administration and the duration of the treatment. The frequency of administration of the polypeptide may vary depending on the severity of the disease. For example, the polypeptide is administered once every 3 months, once every 3 months, once every 2 months, once every month, twice per month or three times per month. The polypeptide can be also administrated daily, twice a day, or more. Under certain conditions the polypeptide is administered continuously. The period of time over which the polypeptide is administered, can vary, depending on any of a variety of factors, e.g., severity of the diseases, age of patient and response of the patient to the treatment.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

FIG. 1 shows the schematic representation of Apelin-77, Apelin-36, Apelin-17 and Apelin-13 (A) and the sequences of Apelin-77 in various animal species.

FIG. 2: Human apelin cDNA encodes a protein of 77 amino acid residues. Newly synthesized apelin is a preproprotein that is proteolytically processed in order to generate mature 36, 17 and 13 amino acid forms. We cloned human apelin into pIRES2-eGFP vector adding a V5 tag in C-terminus of the apelin sequence. Upon examination of the amino acid sequence of the apelin precursor, two dibasic motifs were recognized by the proprotein convertases (PCs) (RRK and FRRQR) suggesting the involvement of these convertases in the maturation of apelin. To identify the PCs involved in apelin processing, apelin and each of the PCs were transiently co-expressed in LoVo cells, a furin-deficient cell line. Supernatants were collected 24 hours after transfection and analyzed for proapelin processing by immunoblotting using a V5 antibody. As illustrated in (a), analyses of media derived from LoVo cells cotransfected with vector encoding proapelin and control vector show a band with an apparent molecular mass of 8-9 kDa, corresponding to the intact apelin precursor. Cotransfection of cells with apelin and vectors encoding different convertase (furin, PACE4, PC5 or PC7) revealed that only the expression of furin is associated with a reduction in the level of the immunoreactive precursor with a concomitant appearance of 2 products of 3-4 and 2-3 kDa, corresponding to apelin-17 and apelin-13.

Figure 3:
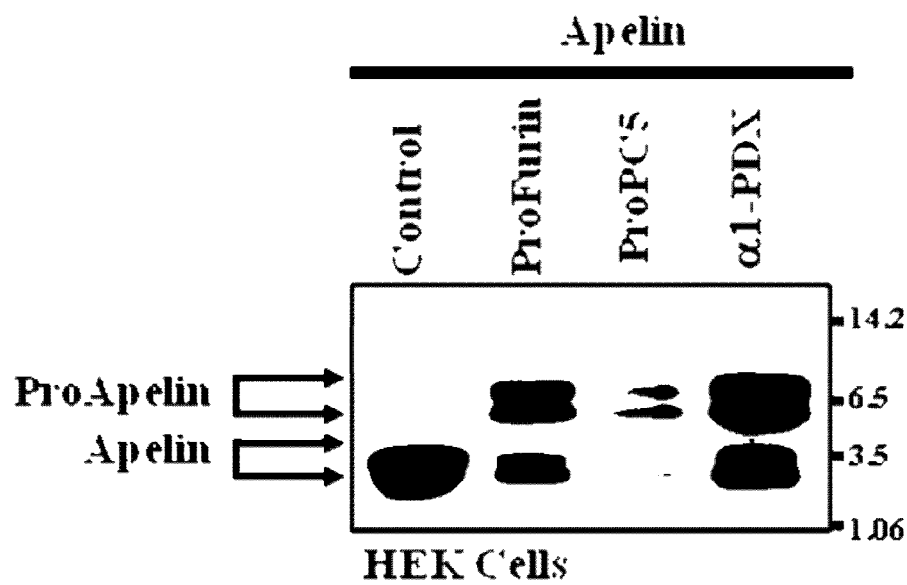

FIG. 3: Expression in HEK293 cells apelin and/or PCs inhibitors the PCs prosegments (profurin, proPC5) and the furin-motif variants of α1-antitrypsin (α1-PDX) indicates that the expression in HEK293 cells with apelin alone resulted in 100% processing, wheaes, cotransfection of cells with apelin and PCs inhibitors inhibited the processing of apelin.

Figure 4:
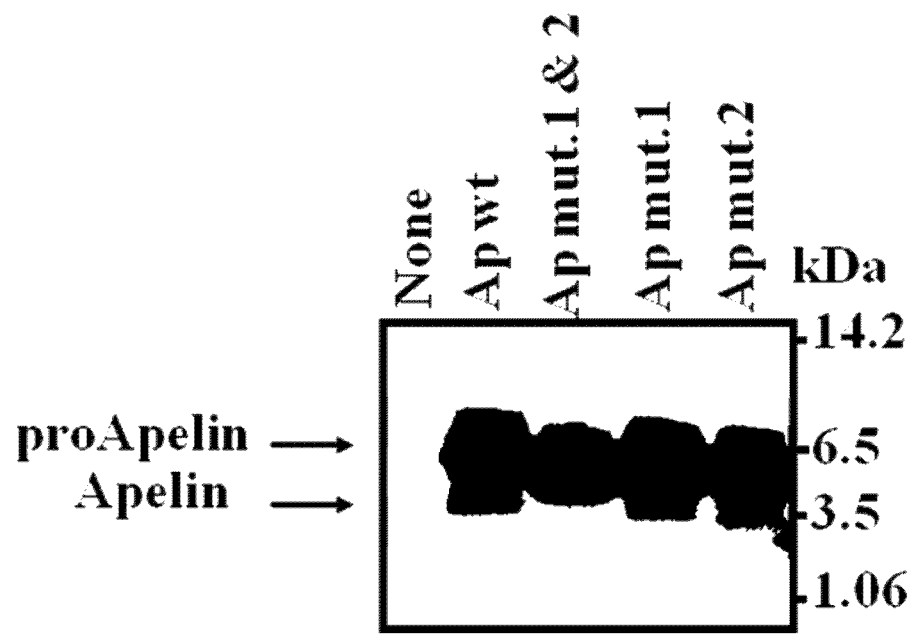

FIG. 4: HEK293 cells were transfected with wild-type or mutants apelin (mut1, mut 2), and media derived from these cells were analyzed by Western blotting. The mutation 1 (mut1) indicates a mutation at the first cleavage site of Apelin (RR60K) and the mutation 2 (mut2) indicates a mutation at the second cleavage site of apelin (RR64QR). Expression of these cells with wild type Apelin, mut1 or mut2 dont affect the processing of Apelin. Whrears the expression in these cells of Apelin with two mutated sites prevented the processing of Apelin. Only the unprocessed form is detected under these conditions.

Figure 5:
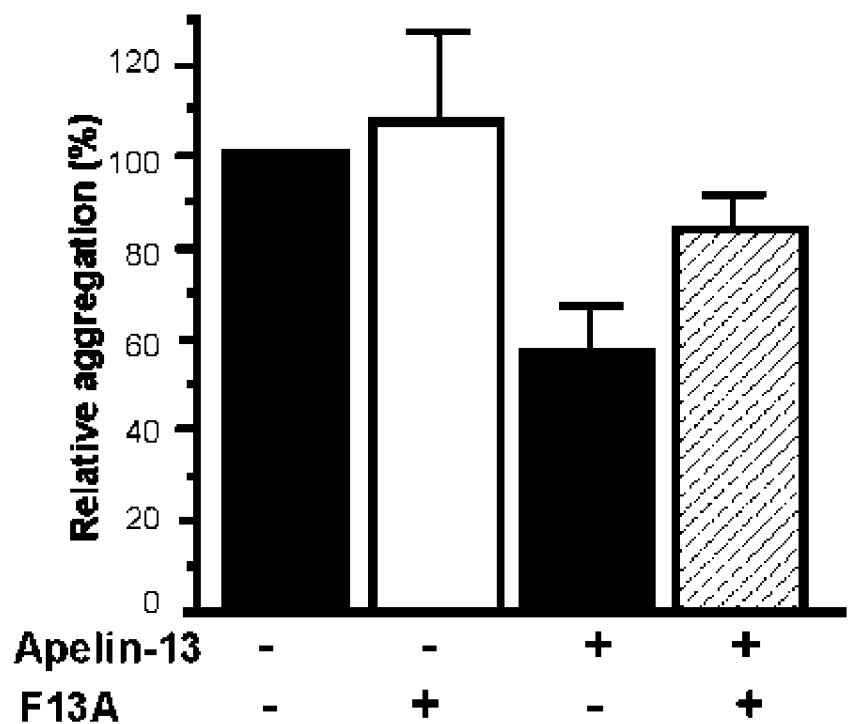

FIG. 5: APJ antagonist (F13A) and unprocessed double mutant apelin-36 (apelin-DM) confirm the role of APJ in the inhibition of platelet function by apelin. Thrombin-induced aggregation of human platelets preincubated with PBS, as control (black bar); F13A (100 nM; white bar); apelin (10 nM; grey bar) or F13A (100 nM) plus apelin (10 nM) (dashed bar).

Figure 6:
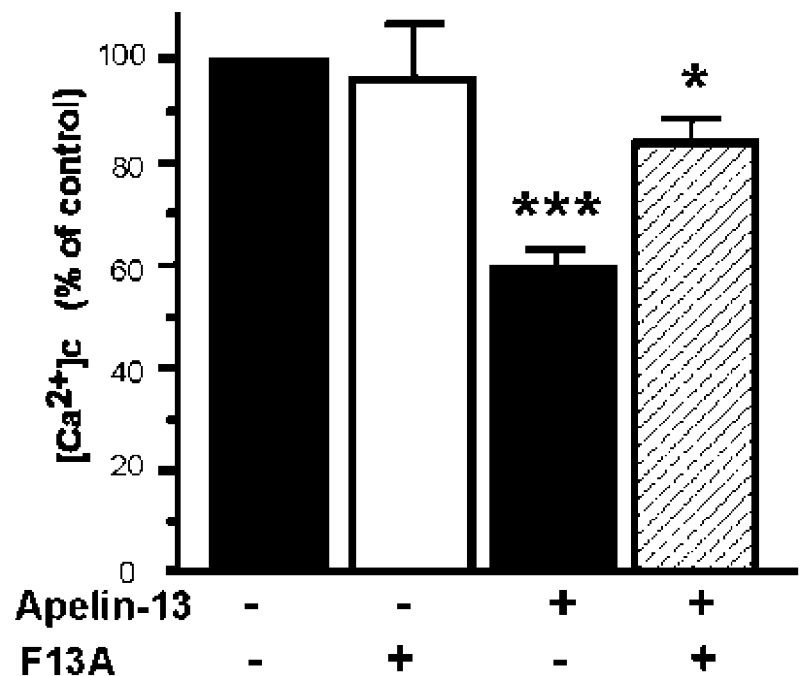

FIG. 6: APJ antagonist (F13A) and unprocessed double mutant apelin-36 (apelin-DM) confirm the role of APJ in the inhibition of platelet function by apelin. Intracellular $Ca^{2+}$ mobilization ($[Ca^{2+}]_i$) in human platelets was monitored in real-time using a fluorescence spectrophotometer. Human platelets, loaded with Fura-2-AM were preincubated 3 minutes with PBS, as control (black bar); F13A (100 nM; white bar); apelin (10 nM; grey bar) or F13A (100 nM) plus apelin (10 nM) (dashed bar) before stimulation by thrombin (100 mU/mL). While F13A alone has no effects on tail bleeding time, platelet aggregation and $Ca^{2+}$ mobilization, its injection with apelin prevents the inhibitory effects of apelin alone.

Figure 7:
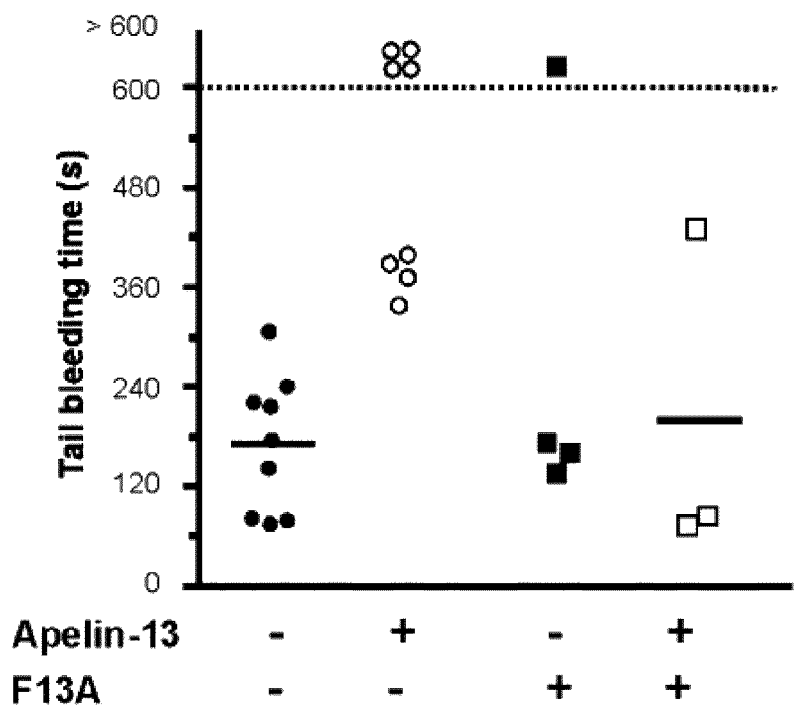

FIG. 7: APJ antagonist (F13A) and unprocessed double mutant apelin-36 (apelin-DM) confirm the role of APJ in the inhibition of platelet function by apelin. Tail bleeding time in wild-type mice receiving an intravenous injection of PBS, as control (●); F13A (500 nmol/kg; ■); apelin (50 nmol/kg; ○) or F13A (500 nmol/kg) plus apelin (50 nmol/kg) (□).

Figure 8:
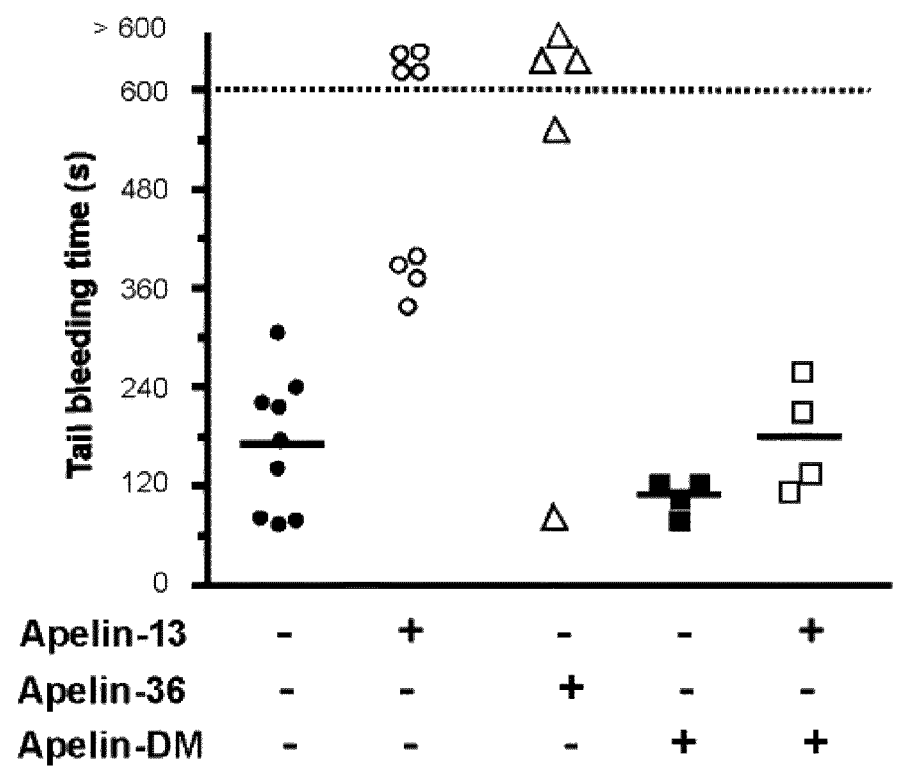

FIG. 8: APJ antagonist (F13A) and unprocessed double mutant apelin-36 (apelin-DM) confirm the role of APJ in the inhibition of platelet function by apelin. Tail bleeding time in wild-type mice receiving an intravenous injection of PBS, as control (●); apelin (50 nmol/kg; ○); apelin-36 (500 nmol/kg; △); apelin-DM (500 nmol/kg; ■), apelin-36 plus apelin (▼) or apelin-DM plus apelin (□).

Figure 9:
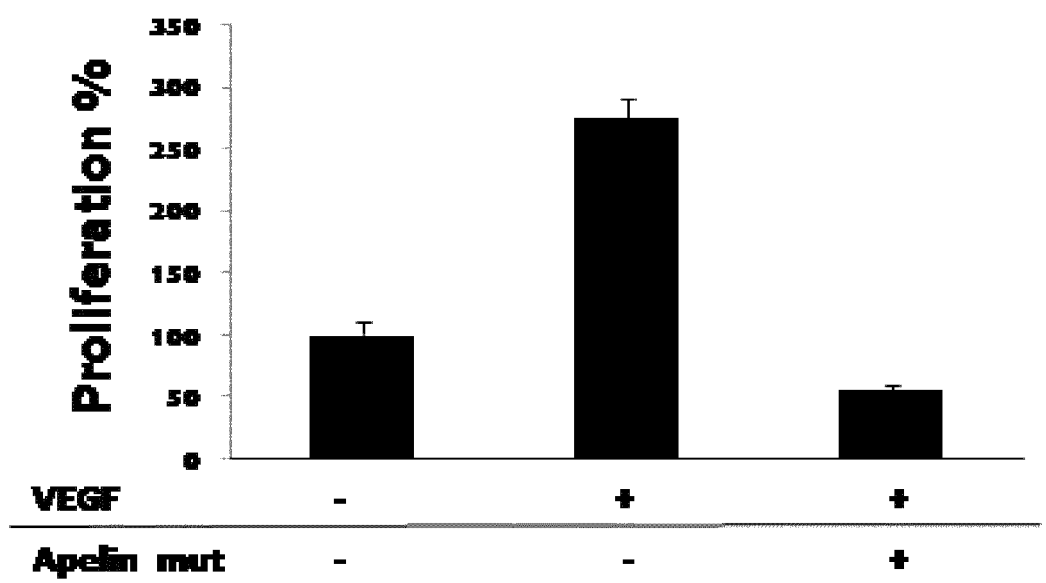

FIG. 9: HUVEC proliferation and motility. HUVEC were serum deprived overnight and then treated for 24 h with or without VEGF in the presence of apelin wild-type (10 ng/ml) and/or apelin mut-36 (10 ng/ml). Cell proliferation was assessed using Cell Titer96 non-radioactive cell proliferation assay.

EXAMPLE 1

Methods

Unprocessed Mutant Apelin (Apelin-DM) Peptide Synthesis:

The unprocessed mutant of apelin (apelin-DM) was synthesized by Eurogentec. During peptide synthesis the two cleavage sites of proapelin ($_{18}$RRKFRR) were replaced by $_{18}$SSKFSS amino acid sequence to generate the apelin-DM mutant peptide:

(SEQ ID NO: 8)
LVQPRGSRNGPGPWQGGSSKFSSQRPRLSHKGPMPF.

Preparation of Washed Platelets:

Human Platelets

Venous blood was collected from healthy donors on 10% (v/v) trisodium citrate (3.8%). Written informed consent was obtained from all the donors. Platelet-rich plasma (PRP) was obtained by centrifugation (120 g; 15 minutes; 20° C.) and platelets were isolated by differential centrifugation as previously described[15]. The platelet pellet was resuspended in modified Tyrode-HEPES buffer without $CaCl_2$ (137 mM NaCl, 2 mM KCl, 0.3 mM $NaH_2PO_4$, 5.5 mM glucose, 5 mM Hepes, 12 mM $NaHCO_3$, pH 7.3).

Mouse Platelets

Mice were anesthetized by intraperitoneal injection of sodium pentobarbital (60 mg/kg). Xylocain® (0.5% v/v) was used as a local analgesic. Whole blood was collected by cardiac puncture and mixed with 80 µM PPACK and 10% (v/v) ACD-C buffer (124 mM sodium citrate, 130 mM citric acid, 110 mM dextrose, pH 6.5) to prevent coagulation. Platelet-rich plasma (PRP) was obtained by centrifugation whole blood for 7 minutes at 160 g. Platelets were obtained from PRP by centrifugation for 10 minutes at 670 g and washed in the presence of apyrase (100 mU/mL) and PGE, (1 µM) to minimize platelet activation, then resuspended in modified Tyrode-HEPES buffer without $CaCl_2$[16].

Haematological Analysis and Bleeding Time:

Complete blood counts and haematocrit were determined with an automatic cell counter, using the standard parameters for mice. Bleeding time assays were performed on overnight fasted animals, after injection of PBS, apelin-13, apelin-36, apelin-DM or F13A into the retro-orbital plexus, by cutting off the tip of the tail (3 mm from the tip) and immediately immersing it in saline at 37° C. We then recorded the time taken for the bleeding to stop. Tail bleeding was monitored for at least 60 seconds beyond this time point, to ensure that bleeding did not begin again. Tail bleeding assays were stopped at 600 seconds if the bleeding did not stop.

Platelet Aggregation:

Platelet aggregation was monitored by measuring light transmission through the stirred suspension of washed platelets ($3\times10^8$/mL) at 37° C. in presence of 1 mM $CaCl_2$ using a Chronolog aggregometer (Chrono-log Corporation, USA). When mentioned, platelets were first incubated with apelin-13, apelin-36, apelin-DM or F13A for 3 minutes at 37° C. Platelet aggregation was triggered by adding collagen, thrombin, or ADP. Representative traces for aggregation were obtained from at least three independent experiments. Results are expressed as the percent change in light transmission with respect to the blank (buffer without platelets), set at 100%.

In Vitro Thrombus Formation Under Flow Conditions:

Thrombus formation was evaluated in a whole-blood perfusion assay on a fibrillar collagen matrix under arterial shear conditions (shear rate of 1000 $s^{-1}$) as previously described[16]. Briefly, glass microcapillary tubes (Vitrocom Hollow Rectangle capillaries; Fiber Optic Center, New Bedford, Mass.) were coated with fibrillar collagen (50 µg/mL; overnight; 4° C.). Blood samples were collected in 80 µM PPACK, fluorescently labelled with rhodamine 6G (10 µg/mL) and incubated for 5 minutes with PBS or apelin-13. Labelled whole blood was then perfused through the coated glass microcapillary with a KD Scientific syringe pump (Fisher Bioblock Scientific, Illkirch, France). Real-time thrombus formation was recorded with an inverted epifluorescence microscope (Nikon Eclipse TE2000-U; Champigny sur Marne, France), coupled to Metamorph 7.0r1 software (Universal Imaging Corporation). Thrombus formation was determined as the mean fluorescence intensity (MFI).

Measurement of Intracellular Free $Ca^{2+}$ Concentration ($[Ca^{2+}]_i$):

Human platelets were loaded with Fura-2 by incubation with 2 µM Fura-2-AM for 45 minutes at 37° C. Cells were then collected by centrifugation at 350 g for 15 min and resuspended in HEPES-buffered saline (145 mM NaCl, 10 mM HEPES, 10 mM D-glucose, 5 mM KCl, 1 mM $MgSO_4$, pH 7.4), and supplemented with 0.1% (w/v) BSA. Fluorescence was recorded from 2 mL aliquots of magnetically stirred cell suspensions at 37° C. using a fluorescence spectrophotometer (Varian Ltd., Madrid, Spain) with excitation wavelengths of 340 and 380 nm and emission at 505 nm. Changes in $[Ca^{2+}]_i$ were monitored using the Fura-2 340/380 fluorescence ratio and calibrated according to the method of Grynkiewicz et al.[19]. $Ca^{2+}$ release by thrombin was estimated using the integral of the rise in $[Ca^{2+}]_i$ for 2.5 minutes after its addition, taking a sample every second, and was expressed in nM as previously described[20].

Statistical Analysis:

Statistical significance was evaluated with Student's t tests, two-tailed Mann-Whitney U-tests or 1-way ANOVA followed by Turkey test as indicated, using GraphPad Prism statistical software (San Diego, Calif.).

Results:

Identified as the endogenous ligand of APJ, a ubiquitously expressed G protein coupled receptor; Apelin exerts multiple physiological effects in the cardiovascular system, fluid homeostasis, and adipoinsular axis. Deregulation of Apelin expression and/or activity was linked to various diseases, including heart failure, atherosclerosis, type 2 diabetes, and obesity. However, the mechanism and function of Apelin precursor (proApelin) conversion to mature Apelin peptides namely: apelin-36, apelin-17 and apelin-13 are not well known (FIG. 1). After removal of the signal peptide, the proteolytic cleavages of proApelin occur within basic motifs, suggesting the involvement of proprotein convertase (PC) family members in this process. Using cell transfection experiments, the processing of proApelin was found to be inhibited by the Furin inhibitors serpin alpha1-antitrypsin (alpha1-PDX) and prosegment proFurin (ppFurin) and proPC5 (ppPC5). Site-directed mutagenesis analysis confirmed the RR(60)KF and KFRR(64)QR preApelin cleavage sites (FIG. 1A). In parallel, the lack of proApelin processing found in the PC activity-deficient cell line LoVo was restored by the expression of Furin, but not by paired basic amino acid cleaving enzyme 4 (PACE4), PC5 or PC7 (FIG. 2).

To investigate the effect of the mutant Apelin peptide (DM) on Apelin functions, we analyzed its role on the recently identified function of apelin on platelet aggregation. Pretreatment of human platelet by thrombin induced their aggregation and Ca2+ mobilisation. In the presence of mature apelin-13 or proApelin (Apelin-36), these platelet functions were inhibited. Whereas platelet incubation with the APJ receptor antagonist apelin-13 (F13A) and the synthetic unprocessed double mutant Apelin peptide (Apelin-DM) abolished the apelin inhibitory effect on thrombin-induced aggregation and Ca2+ mobilisation (FIG. 4). Accordingly, using mice tail-bleed assay, we found that intravenous injection of apelin-13 or Apelin-36 induced a significant increase in bleeding time. This effect was inhibited by F13A and Apelin-DM (FIG. 5). The use of RT-PCR and immunoblotting analysis revealed that human platelet express apelin and its receptor APJ, at the RNA and protein levels. In these cells the furin was also expressed. Our findings demonstrate the processing of Apelin by furin and highlight the potential use of unprocessed mutant Apelin peptide as agent for metabolic disorders treatment through platelet aggregation inhibition that possess a functional apelin/APJ system.

EXAMPLE 2

We found that the synthetic apelin mutant peptide (SEQ ID NO: 8) inhibits endothelial cell proliferation and migration induced by VEGF (FIG. 5).

Using synthetic active apelin-13 and unprocessed mutant apelin we found that while apelin-13 induced the formation of new vessels, the latter prevents the neo-vascularisation as assessed by the chick chorioallantoic membrane (CAM) and mouse aortic ring assays. In conclusion while active apelin-13 aa induced the formation of new vessels, the addition of the unprocessed mutant apelin blocked this process.

Similarly, the use of the cutaneous reverse passive Arthus reactions assay revealed that while apelin increased tissue inflammation, the mutant unprocessed apelin inhibited these processes.

Taken together, these findings indicate the ability of the apelin mutant peptide to mediate in vitro and in vivo biological actions. We now evaluate the potential use of this newly identified inhibitor and/or derivates in tumor angiogenesis and lymphangiogenesis therapy.

The invention claimed is:

1. A polypeptide comprising the sequence as set forth in SEQ ID NO:1 wherein each of the arginine residues at positions 18, 19, 22 and 23 have been substituted by a serine residue.

2. The polypeptide according to claim 1 which comprises a sequence as set forth in SEQ ID NO:2 wherein each of the arginine residues at positions 59, 60, 63, and 64 have been substituted by a serine residue.

3. A method of inhibiting angiogenesis in a subject in need thereof comprising
administering to the subject a polypeptide comprising a sequence as set forth in SEQ ID NO:1 wherein each of the arginine residues at positions 18, 19, 22 and 23 have been substituted by a serine residue.

4. The method of claim 3, wherein the subject has cancer.

5. A method of producing a polypeptide comprising the steps of:
(i) culturing a transformed host cell comprising I) a nucleic acid comprising a sequence encoding a polypeptide comprising the sequence as set forth in SEQ ID NO:1 wherein each of the arginine residues at positions 18, 19, 22 have 23 has been substituted by a serine residue, or II) a vector comprising the nucleic acid, said step of culturing being carried out under conditions suitable to allow expression of said polypeptide; and
(ii) recovering the expressed polypeptide.

* * * * *

SEQUENCE LISTING

```
<160> NUMBER OF SEQ ID NOS: 8

<210> SEQ ID NO 1
<211> LENGTH: 36
<212> TYPE: PRT
<213> ORGANISM: Homo sapiens

<400> SEQUENCE: 1

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe
        35

<210> SEQ ID NO 2
<211> LENGTH: 77
<212> TYPE: PRT
<213> ORGANISM: Homo sapiens

<400> SEQUENCE: 2

Met Asn Leu Arg Leu Cys Val Gln Ala Leu Leu Leu Leu Trp Leu Ser
1               5                   10                  15

Leu Thr Ala Val Cys Gly Gly Ser Leu Met Pro Leu Pro Asp Gly Asn
            20                  25                  30

Gly Leu Glu Asp Gly Asn Val Arg His Leu Val Gln Pro Arg Gly Ser
        35                  40                  45

Arg Asn Gly Pro Gly Pro Trp Gln Gly Gly Arg Arg Lys Phe Arg Arg
    50                  55                  60

Gln Arg Pro Arg Leu Ser His Lys Gly Pro Met Pro Phe
65                  70                  75

<210> SEQ ID NO 3
<211> LENGTH: 77
<212> TYPE: PRT
<213> ORGANISM: Mus musculus

<400> SEQUENCE: 3

Met Asn Leu Arg Leu Cys Val Gln Ala Leu Leu Leu Leu Trp Leu Ser
1               5                   10                  15

Leu Thr Ala Val Cys Gly Val Pro Leu Met Leu Pro Pro Asp Gly Thr
            20                  25                  30

Gly Leu Glu Glu Gly Ser Met Arg Tyr Leu Val Lys Pro Arg Thr Ser
        35                  40                  45

Arg Thr Gly Pro Gly Ala Trp Gln Gly Gly Arg Arg Lys Phe Arg Arg
    50                  55                  60
```

Gln Arg Pro Arg Leu Ser His Lys Gly Pro Met Pro Phe
65                  70                  75

<210> SEQ ID NO 4
<211> LENGTH: 77
<212> TYPE: PRT
<213> ORGANISM: Rattus norvegicus

<400> SEQUENCE: 4

Met Asn Leu Ser Phe Cys Val Gln Ala Leu Leu Leu Trp Leu Ser
1               5                   10                  15

Leu Thr Ala Val Cys Gly Val Pro Leu Met Leu Pro Pro Asp Gly Lys
                20                  25                  30

Gly Leu Glu Glu Gly Asn Met Arg Tyr Leu Val Lys Pro Arg Thr Ser
            35                  40                  45

Arg Thr Gly Pro Gly Ala Trp Gln Gly Gly Arg Arg Lys Phe Arg Arg
        50                  55                  60

Gln Arg Pro Arg Leu Ser His Lys Gly Pro Met Pro Phe
65                  70                  75

<210> SEQ ID NO 5
<211> LENGTH: 77
<212> TYPE: PRT
<213> ORGANISM: Bos taurus

<400> SEQUENCE: 5

Met Asn Leu Arg Arg Cys Val Gln Ala Leu Leu Leu Trp Leu Cys
1               5                   10                  15

Leu Ser Ala Val Cys Gly Gly Pro Leu Leu Gln Thr Ser Asp Gly Lys
                20                  25                  30

Glu Met Glu Glu Gly Thr Ile Arg Tyr Leu Val Gln Pro Arg Gly Pro
            35                  40                  45

Arg Ser Gly Pro Gly Pro Trp Gln Gly Gly Arg Arg Lys Phe Arg Arg
        50                  55                  60

Gln Arg Pro Arg Leu Ser His Lys Gly Pro Met Pro Phe
65                  70                  75

<210> SEQ ID NO 6
<211> LENGTH: 77
<212> TYPE: PRT
<213> ORGANISM: Brachybacterium alimentarium

<400> SEQUENCE: 6

Met Asn Val Lys Ile Leu Thr Leu Val Ile Val Leu Val Val Ser Leu
1               5                   10                  15

Leu Cys Ser Ala Ser Ala Gly Pro Met Ala Ser Thr Glu His Ser Lys
                20                  25                  30

Glu Ile Glu Glu Val Gly Ser Met Arg Thr Pro Leu Arg Gln Asn Pro
            35                  40                  45

Ala Arg Ala Gly Arg Ser Gln Arg Pro Ala Gly Trp Arg Arg Arg Arg
        50                  55                  60

Pro Arg Pro Arg Leu Ser His Lys Gly Pro Met Pro Phe
65                  70                  75

<210> SEQ ID NO 7
<211> LENGTH: 77
<212> TYPE: PRT
<213> ORGANISM: Carassius auratus

```
<400> SEQUENCE: 7

Met Asn Val Lys Ile Leu Thr Leu Val Ile Val Leu Val Val Ser Leu
1               5                   10                  15

Leu Cys Ser Ala Ser Ala Gly Pro Met Ala Ser Thr Glu His Ser Lys
                20                  25                  30

Glu Leu Glu Glu Val Gly Ser Met Arg Thr Pro Leu Arg Gln Asn Pro
            35                  40                  45

Ala Arg Ala Gly Arg Ser Gln Arg Pro Ser Gly Trp Arg Arg Arg Arg
        50                  55                  60

Pro Arg Pro Arg Leu Ser His Lys Gly Pro Met Pro Phe
65                  70                  75

<210> SEQ ID NO 8
<211> LENGTH: 36
<212> TYPE: PRT
<213> ORGANISM: Artificial
<220> FEATURE:
<223> OTHER INFORMATION: Synthetic inhibitor of apelin

<400> SEQUENCE: 8

Leu Val Gln Pro Arg Gly Ser Arg Asn Gly Pro Gly Pro Trp Gln Gly
1               5                   10                  15

Gly Ser Ser Lys Phe Ser Ser Gln Arg Pro Arg Leu Ser His Lys Gly
                20                  25                  30

Pro Met Pro Phe
            35
```